US00PP16935P2

(12) United States Plant Patent
Utecht

(10) Patent No.: US PP16,935 P2
(45) Date of Patent: Aug. 1, 2006

(54) ***PELARGONIUM* PLANT NAMED 'FISMORED'**

(50) Latin Name: *Pelargonium×hortorum*
Varietal Denomination: Fismored

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 22 days.

(21) Appl. No.: 11/167,678

(22) Filed: Jun. 27, 2005

(51) Int. Cl.
*A01H 5/00* (2006.01)

(52) U.S. Cl. ..... Plt./325

(58) Field of Classification Search ..... Plt./325
See application file for complete search history.

*Primary Examiner*—Kent Ball
(74) *Attorney, Agent, or Firm*—Jondle & Associates P.C.

(57) ABSTRACT

A new cultivar of *Pelargonium* particularly characterized by the combined features of light salmon-colored flowers with a brilliant-red-striped pattern on the petals, large inflorescences well above the foliage, strong peduncles, medium-green-colored nearly round leaves with strong zonation, a medium to tall plant habit, a mid-season flowering response and having good weather resistance is disclosed.

1 Drawing Sheet

Figure 1:
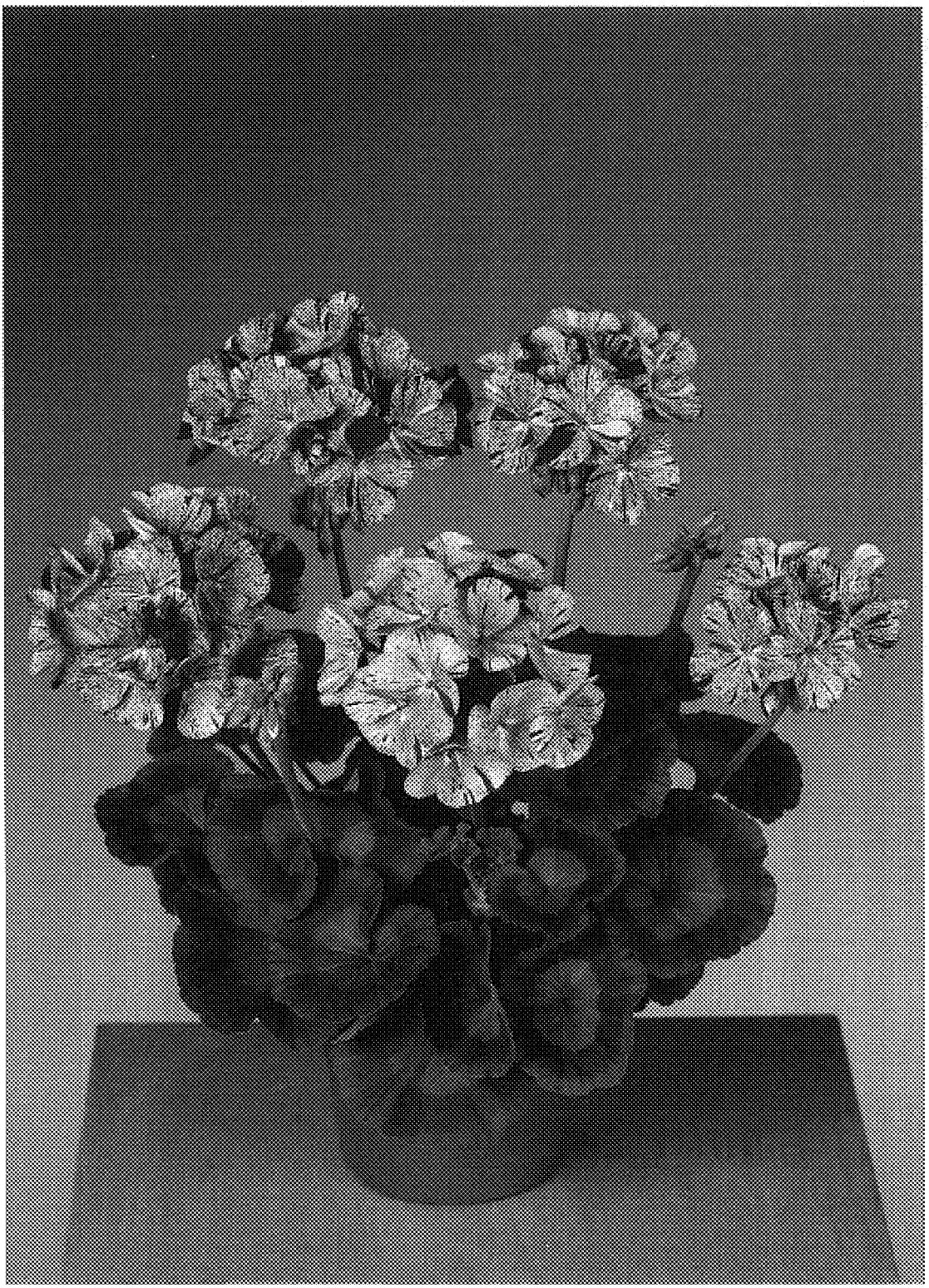

Genus and species: *Pelargonium×hortorum.*
Variety denomination: 'Fismored'.

BACKGROUND OF THE NEW PLANT

The present invention comprises a new and distinct cultivar of *Pelargonium*, botanically known as *Pelargonium× hortorum*, resp. a hybrid of *Pelargonium zonale* L'Héritier and hereinafter referred to by the cultivar name 'Fismored'. The new cultivar is a product of a planned breeding program which had the objective of creating new varieties having speckled or striped flower color and good outdoor performance. 'Fismored' was discovered as a seedling resulting from a cross between the female parent, 'Starburst Red' (U.S. Plant Pat. No. 9,229), which has white and red striped, single-type flowers and the male parent, hybrid seedling No. k94-2020-4 (unpatented), which has salmon-colored single-type flowers, medium green foliage with strong zonation, and vigorous growth.

The new cultivar was created in 2000 in Hillscheid, Germany, and has been asexually reproduced repeatedly by vegetative cuttings in Galdar, Gran Canaria, Spain, and Hillscheid, Germany, over a four-year period. 'Fismored' has not been observed under all possible environmental conditions, thus, the phenotype may vary significantly with variations in the environment such as temperature, light intensity, and day length. It has been found to retain its distinctive characteristics through successive asexual propagations. 'Fismored' reproduces true to type in successive generations of asexual reproduction.

SUMMARY OF THE INVENTION

The following are the most outstanding and distinguishing characteristics of the new cultivar when grown under normal commercial practices in Hillscheid, Germany.

1. Single-type flowers of mainly light salmon ground color, with a pattern of red stripes and dots and good stability of flower color;
2. Relatively large inflorescences on strong peduncles well above the foliage;

3. Medium-green foliage, large round leaves with strong zonation;
4. Medium to tall plant with vigorous growth;
5. A mid-season flowering response; and
6. Good rain resistance with a relatively slight tendency to shatter for a single-type variety.

DESCRIPTION OF PHOTOGRAPH

This new *geranium* plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings, in 14-cm pots, left un-pinched, and grown under greenhouse conditions which approximate those generally used in commercial practice.

FIG. 1. shows overall plant habit with blooms, buds, and foliage.

DESCRIPTION OF THE NEW CULTIVAR

The following detailed descriptions set forth the distinctive characteristics of 'Fismored'. The data which define these characteristics were collected from asexual reproductions carried out in Hillscheid, Germany. The plant history was taken on twelve-week-old, un-pinched plants in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.—Pelargonium×hortorum*, resp. a hybrid of *Pelargonium zonale* L'Héritier.

*Common name.—Geranium.*

*Parentage*.—Female parent: 'Starburst Red' (U.S. Plant Pat. No. 9,229). Male parent: Hybrid seedling No. k94-2020-4 (unpatented).

Plant:

*Form*.—Shrub, self-branching, surface of foliage canopy rounded, and is moderately tight.

*Branching habit*.—About 5.7 branches per plant.

*Height*.—14.3 cm for a 9 week-old plant (measured from base of stem to the tips of the branches, excluding the inflorescences).

*Width*.—23.8 cm for a 9 week-old plant.

*Time to produce a finished flowering plant*.—For spring flower response in Hillscheid, Germany, in 2004, 50% of the plants had open flowers after 9 weeks.

*Outdoor plant performance*.—Plants continuously flower; a flower count in mid May of 2004 in Hillscheid, Germany indicated about 2 inflorescences per plant.

Leaves:

*Arrangement*.—Alternate.

*Mature leaf*.—Color: Upper surface: RHS 143A (medium green). Lower surface: RHS 138A to RHS 138B. Length: 6.3 cm. Width: 10.2 cm.

*Zonation color*.—Strong RHS 166A (brown).

*Zonation diameter*.—Inner diameter is 5.2 cm while the belt of zonation is 2.5 cm wide.

*Apex*.—Rounded.

*Base*.—Cordate.

*Shape*.—Nearly round with no lobes, margin is slightly wavy (comparatively little), with the lowest lobes overlapping.

*Margin*.—Bi-crenate.

*Texture*.—Upper surface is smooth, dull, and velvety.

Petioles:

*Length*.—6.0–8.0 cm.

*Diameter*.—0.3 cm.

*Color*.—RHS 143C (light-green).

*Texture*.—Covered by short, weak pubescence.

Stems:

*Length*.—6.0–9.0 cm.

*Internode length*.—1.0–1.5 cm.

*Color*.—RHS 143B (green).

*Texture*.—Appears smooth with weak pubescence.

Flower buds:

*Length*.—2.1 cm.

*Width*.—0.9 cm.

*Shape*.—Narrow and elliptical.

*Color of sepals* (*just before petals unfold*).—RHS 144A (light-green).

*Color of petals* (*just before petals unfold*).—Mainly RHS 49D with RHS 44C (orange-red) markings.

Inflorescence:

*Type*.—An umbel composed of 25–35 flowers.

*Umbel diameter*.—10.0 cm.

*Umbel depth* (*height*).—6.2 cm.

*Umbel shape*.—Semi-spherical.

*Lastingness of umbel on the plant*.—About 18 days.

*Peduncle*.—Length: 14.2 cm. Diameter: 4.0–5.0 mm. Texture: Very short pubescence. Color: RHS 143C (light-green) with occasionally a slight tinge of RHS N170A (brown).

*Pedicel*.—Length: 3.1 cm, with spur. Diameter: 1.5 mm. Texture: Very weak pubescence. Color: RHS 144C (light-green).

Corolla:

*Diameter*.—4.7 cm.

*Form*.—Single-type.

*Shape*.—Round outline, weakly cup-shaped.

*Number of petals*.—5.

*Number of petaloids*.—None.

*Lastingness of individuals flowers on the plant*.—7–8 days at 18° C.

*Fragrance*.—None.

Petals:

*Upper petals*.—Length: 2.6–2.7 cm. Width: 2.2–2.4 cm. Color: Upper surface: Mainly RHS 43D (salmon-pink) with areas of RHS 69A. Lower surface: Mainly RHS 49D, with RHS 44C to RHS 44D (orange-red) stripes or macules. Markings: Orange-red stripes, dots, or sections on the petal, ranging from RHS 44A to RHS 44B.

*Lower petals*.—Length: 2.4–2.5 cm. Width: 2.4–2.6 cm. Color: Upper surface: Mainly RHS 43D (salmon-pink) with areas of RHS 69A. Lower surface: Mainly RHS 49D, with RHS 44C to RHS 44D (orange-red) stripes or macules. Markings: Orange-red stripes, dots, or sections on the petal, ranging from RHS 44A to RHS 44B.

*Shape*.—Obovate.

*Apex*.—Rounded.

*Base*.—Acute.

*Margin*.—Entire.

*Texture*.—Smooth, glabrous, and slightly glossy.

Sepals:

*Number*.—5.

*Length*.—1.0–1.2 cm.

*Width*.—0.5 cm for the largest upper sepal and 0.3 cm for the other sepals.

*Shape*.—Linear to lanceolate.

*Apex*.—Acute.

*Margin*.—Entire.

*Base*.—Truncate.

*Texture*.—Very weak pubescence.

*Color*.—RHS 144C (light-green) for both upper and lower surfaces.

Reproductive organs:

*Androecium*.—Number of anthers: 7. Filament color: RHS 155D (white) to RHS 43B near upper end. Filament length: 6.0–8.0 mm. Pollen color: RHS 28A (yellow-orange). Pollen amount: Abundant.

*Gynoecium*.—Number: 1. Pistil length: 8.0 mm. Stigma color: RHS 43C (salmon-pink). Stigma shape: 5–6 lobed. Style color: RHS 43C (salmon-pink). Style length: 3.0–4.0 mm. Style shape: Filiform, filament-like, with the lobes of the stigma at right angles.

Fruit/seed set: No seed set observed.

Disease and insect resistance: Average/typical for the species and not very susceptible to *Botrytis,* due to the open, single-type flowers and the almost flat, hardly wavy leaves.

COMPARISON WITH KNOWN CULTIVARS

Of the many commercial cultivars known to the present inventor, the most similar in comparison to 'Fismored' are the varieties 'Starburst Red' (U.S. Plant Pat. No. 9,229) and 'Amri Conred' (U.S. Plant Pat. No. 15,880).

Cultivar 'Fismored' differs from the female parent 'Starburst Red' (U.S. Plant Pat. No. 9,229) in that the inflorescences of 'Fismored' are borne higher above the foliage, and it has somewhat smaller leaves of more intense green color.

Cultivar 'Fismored' differs from the male parent hybrid seedling No. k94-2020-4 (unpatented), in that 'Fismored' has salmon-pink flowers with an orange-red pattern while hybrid seedling No. k94-2020-4 has salmon-colored flowers.

Cultivar 'Fismored' differs from the commercial comparison variety 'Amri Conred' (U.S. Plant Pat. No. 15,880) in that 'Fismored' has more orange-red, not bright-red, colored stripes on the petals, and somewhat longer peduncles. Additionally, the pedicels of 'Fismored' are green, while those of 'Amri Conred' are mainly dark red. Furthermore, the leaf blades of 'Fismored' are almost flat, while those of 'Amri Conred' are wavy, like most zonal varieties.

I claim:

1. A new and distinct cultivar of *Pelargonium* plant as shown and described herein.

* * * * *